United States Patent [19]

Stokes

[11] 4,020,846

[45] May 3, 1977

[54] SPLINTER PULLER

[76] Inventor: Henry W. Stokes, 9 Martin's Cove Lane, Hingham, Mass. 02043

[22] Filed: Sept. 26, 1975

[21] Appl. No.: 617,043

[52] U.S. Cl. .............................. 128/305; 128/354; 81/43; 30/253
[51] Int. Cl.² .................. A61B 17/32; A61B 17/28
[58] Field of Search ............... 30/124, 186, 253; 81/43; 128/305, 354; 401/256

[56]  References Cited
UNITED STATES PATENTS

| 762,848 | 6/1904 | Schoenner | 401/256 |
|---|---|---|---|
| 1,038,164 | 9/1912 | Lobb | 81/43 X |
| 1,286,673 | 12/1918 | Linke | 128/354 |
| 1,785,919 | 12/1930 | Stickel et al. | 128/354 |

FOREIGN PATENTS OR APPLICATIONS

| 1,101,790 | 10/1955 | France | 401/256 |

Primary Examiner—Channing L. Pace
Attorney, Agent, or Firm—Kenway & Jenney

[57] ABSTRACT

An instrument for removing splinters embedded in skin has a pair of pincers that extend generally in a first direction and are mutually spaced apart in a second direction transverse to the first direction. Each pincer is substantially broader in a third direction orthogonal to the first and second directions than in the second direction. A free or working end of each pincer, also broader in the third direction than the second direction, converges convexly to a tip. The leading edges of the working ends, defined by the junction of the interior facing surfaces of the working ends and the outwardly facing exterior surfaces, are sharpened to facilitate the penetration of the instrument to the embedded splinter. The interior facing surfaces of the working ends adjacent the leading edges are preferably hollowed to prevent blocking.

4 Claims, 6 Drawing Figures

SPLINTER PULLER

BACKGROUND OF THE INVENTION

This invention relates in general to medical instruments and more specifically to instruments for removing splinters embedded in the skin.

In general, conventional splinter removal instruments fall into two categories, general purpose, square-ended tweezers and needle-nose tweezers. Standard, general purpose tweezers are designed to pick up small objects from a hard surface. The square configuration of the working end of these tweezers brings a large gripping surface to bear on the object. Such tweezers, however, have numerous disadvantages when used as splinter pullers.

First, the blunt, square ends reach the embedded splinter by displacing the overlying skin which can generate a high degree of trauma, pain and discomfort. Second, the tweezers themselves tend to obscure the visual guidance of the tweezers to the splinter. Third, even when such tweezers are properly positioned to grip the splinter, the gripping ends often fail to grip the splinter reliably and powerfully. One cause of the poor grip is a misalignment or "offset" of the gripping surfaces due to a lateral displacement or twist of the tweezer arms. Another problem, commonly termed "blocking," is that the tweezer arms meet at some point "behind" the gripping ends before the gripping or working ends grasp or firmly grasp the splinter. Because of these problems, standard square-end tweezers are usually effective only for splinters having a substantial portion extending above the skin, but not for splinters embedded in the skin.

Needle-nose tweezers avoid some of the problems associated with standard tweezers in that they more readily penetrate the skin and allow better visual guidance of the tweezers. However, the sharply pointed working ends of needle-nose tweezers also reach the splinter by displacing the overlying skin and therefore can also generate trauma, pain and discomfort. Another disadvantage of needle-nose tweezers is that they are prone to offset, particularly a complete failure of the gripping surfaces to mate as they "pass" one another. Also, since most splinters are fine, elongated objects, it is difficult to position the sharply pointed working ends of the needle-nose tweezers to grip the splinter without the aid of a magnifying device.

It is therefore a principal object of this invention to provide an instrument for removing splinters embedded in skin that readily locates a splinter with a minimum of discomfort and, once located, grips the splinter reliably and powerfully.

A further object of the invention is to provide an instrument for removing splinters that maintains the gripping ends in mating alignment and is not prone to blocking.

SUMMARY OF THE INVENTION

An instrument for removing splinters has a pair of spaced apart pincers secured on an end of a handle. The nose portions or working ends of the pincers are broad in a direction orthogonal to the longitudinal axis of the handle and pincers and to the direction of the spacing between the pincers. Leading edges of each working end that meet at the tip of each pincer have a slight convex curvature and are sharpened to easily penetrate the skin in the manner of a scalpel with a minimum of trauma, pain or discomfort. The leading edges mate when the pincers are flexed together in a gripping movement. The interior facing surfaces of the pincers adjacent the leading edge are hollowed to ensure that the leading edges grip the splinter before other portions of the pincers meet. In a preferred form, the pincers are milled from a single piece of heat treatable steel, the pincers are less than two inches in length, and the working ends extend at least 1/16 inch between the leading edges, except at the tips.

These and other features and objects of the invention will be more fully understood from the following detailed description to be read in conjunction with the accompanying drawings.

DETAILED DESCRIPTION OF THE PREFERRED EMBODIMENTS

Figure 1:
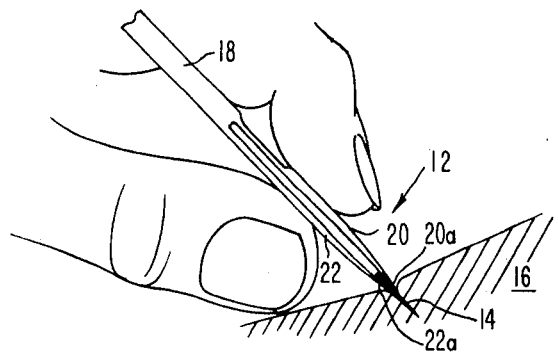
FIG. 1 is a view in perspective of a splinter puller constructed according to the invention gripping a splinter embedded in the skin.

FIG. 1 illustrates a splinter puller 12 constructed according to the invention being used to grip and remove a fine, elongated splinter 14 embedded in a layer of skin 16. The splinter puller 12 is designed to be hand held with an elongated, cylindrical handle portion 18 resting between the thumb and index finger in the manner of a pencil or pen. A pair of spaced apart pincers 20 and 22, secured to one end of the handle 18, are gripped at their opposite exterior surfaces between the thumb and index finger. When the noses or working ends 20a and 22a of the pincers 20 and 22, respectively, have penetrated into the skin and are located on opposite sides of a portion of a splinter 14, the thumb and index finger draw the working ends 20a and 22a towards one another to grip the interposed splinter 14. The splinter is removed by maintaining this gripping relationship as the puller 12 is withdrawn from the skin.

With reference to FIGS. 2-6, the handle 18 and the pincers 20 and 22 extend generally in a first direction, indicated by an arrow 24, along a common longitudinal axis. Pincers 20 and 22 are bridged at their ends adjacent the handle 18 by a base portion 26 which is integral with the pincers. The handle 18 and the base portion 26 can be secured by any suitable means such as threading a portion of the base 26 into the handle 18. The pincers 20 and 22 as well as the base portion 26 are preferably milled from a single piece of heat treatable steel with a longitudinally extending, generally parallel-walled, clearance channel 28 separating the two pincers. The pincers are thus spaced in a second direction, indicated by an arrow 30, in a direction transverse to the first direction.

Figure 3:
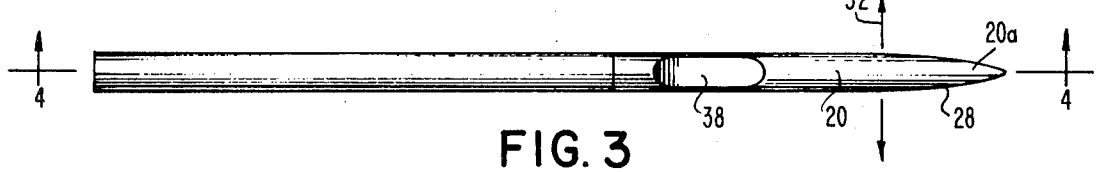
FIG. 3 is a side elevation of the splinter puller shown in FIG. 2.
Figure 4:
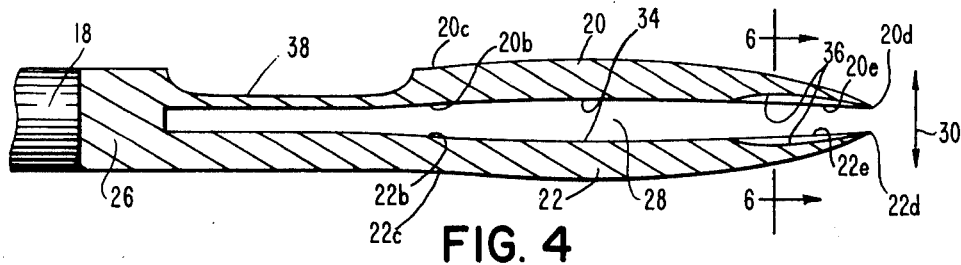
FIG. 4 is an enlarged sectional view of the pincers of the splinter puller in the relaxed position taken along the lines 4—4 of FIG. 3.
Figure 5:
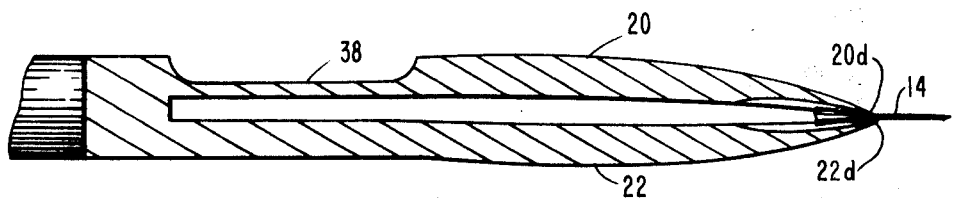
FIG. 5 is a view corresponding to FIG. 4 showing the pincers gripping a splinter.
Figure 6:
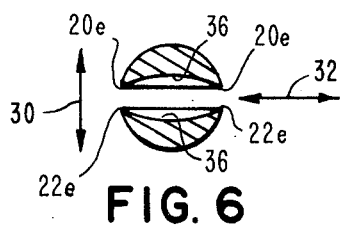
FIG. 6 is a view in vertical section taken along the lines 6—6 of FIG. 4.

Each pincer 20 and 22 has a generally hemicylindrical configuration with the generally flat surfaces 20b and 22b of each pincer forming the interior facing surfaces that define the channel 28. The exterior surfaces 20c and 22c have a curvature generally matching that of the handle 18. At the working ends 20a and 22a the pincers converge or taper to tips 20d and 22d, respectively. As best seen in FIG. 3, the working ends are broad in a third direction (arrow 32) orthogonal to the first and second directions, slightly rounded, and convex. The working ends also converge or taper to the tips 20d and 22d in the second direction as is best seen in FIGS. 4 and 5. This convergence or tapering, in conjunction with the rounded configuration of the exterior surfaces, defines a pair of leading edges 20e and 22e formed at the juncture of the exterior surfaces 20b and 22b with the interior 20c and 22c. The leading edges of each pincer meet at the tips 20d and 22d and extend generally along the working ends 20a and 22a. A significant feature of the invention is that these leading edges are sharpened to slice into the skin in the manner of a scalpel and thereby promote the entry of the working ends into the skin with a minimum of trauma, pain or discomfort. This slicing or cutting action is in sharp contrast to a "head-on" displacement action of square-end or needle-nose tweezers, including needle-nose tweezers having sharply pointed tips.

Figure 2:
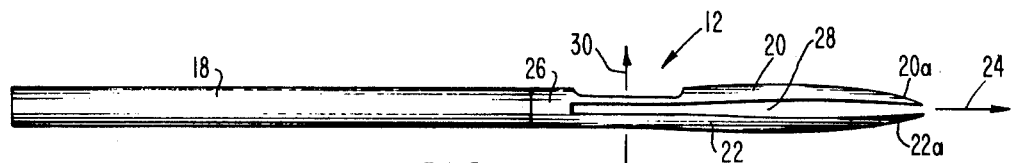
FIG. 2 is a plan view of the splinter puller shown in FIG. 1.

The pincers 20 and 22 are resilient and movable in the second direction between a normal relaxed position illustrated in FIGS. 2 and 4, and a flexed or gripping position illustrated in FIGS. 1 and 5. In the relaxed position, the pincers are generally parallel and the spacing along the channel 28 is generally constant. In the gripping position, one or both of the pincers flex to bring the leading edges 20e and 22e of the working ends into contact with one another or, in use, to grip an interposed splinter 14.

In order to grip the splinter reliably and powerfully, it is important that the opposed working ends 20a and 22a, and in particular the opposed leading edges 20e and 22e, maintain an alignment which brings them into contact with one another when the pincers 20 and 22 are flexed into the gripping position. The splinter puller 12 of this invention maintains this alignment because each of the pincers is significantly broader in the third direction indicated by the arrow 32, than in the second direction indicated by the arrow 30. This relationship also carries into the working ends 20a and 22a. This configuration is highly resistant to misalignment due to transverse forces in the third direction which tends to "offset" the gripping edges. Further, the pincers 20 and 22 are sufficiently thick in the second direction that they effectively resist misalignment due to a twisting about the longitudinal axis sometimes encountered in using square-end tweezers.

To ensure that the pincers 20 and 22 grip the fine splinter 14 with a high degree of force, it is also important to eliminate contact between the pincers at any point other than the leading edges. To reduce the possibility of such a "blocking," the pincers themselves preferably have a slight outward bow as indicated at 34. In addition, the interior surface of the working ends adjacent the leading edges can be formed with a slight concave curvature or hollows 36 as best seen in FIGS. 4 and 5. The hollows 36 can be formed by standard techniques such as grinding. The hollows 36 ensure that the splinter 14 is gripped powerfully, evenly, and reliably between the leading edges of the working ends without blocking by the facing surfaces adjacent to the leading edges.

Preferably one of the pincers (pincer 20 as illustrated) has a thinned region generated by a depression 38 formed on its outer surface over a region adjacent to the base portion 26. This thinned region promotes the flexing or gripping movement of the pincer 20. Because this thinned region makes the pincer 20 significantly more flexible in the second direction than the pincer 22, in the gripping movement the pincer 20 moves towards the pincer 22 which is substantially stationary. This arrangement somewhat facilitates the location of the splinter 14 between the gripping edges.

In addition to the above described advantages, the splinter puller 12 also facilitates locating the embedded splinter. First, as the splinter puller 12 is inserted into the skin, it allows a relatively unobstructed view of the splinter, particularly as compared with conventional square-end tweezers. Second the sharpened leading edges, in cooperation with the tapered, rounded configuration of the working ends, readily cut through the skin overlying the splinter rather than displacing the skin and perhaps the splinter, so that the gripping movement misses the splinter entirely or grips a portion of the skin as well as the splinter. Finally, the broad, rounded edge configuration of the working ends increase the likelihood that the splinter will be gripped between the leading edges, particularly as compared to needle-nose tweezers.

It has been found that in order to maintain sure the proper alignment of the gripping edges, the pincers 20 and 22 should have a length of less than 2 inches and preferably a length of 1¾ inches. In addition, it has been found that the nose working ends 20a and 22a should have a breadth of at least 1/16 inch measured from the leading edges in the third direction, except over a small region immediately adjacent to the tips 20d and 22d. With a pincer length of approximately 1¾ inches, a typical maximum breadth for the pincers in the third direction is approximately 3/16 inch, and a typical maximum thickness in the second direction is 3/32 inch.

Although the invention has been described with the pincers as being milled from a single piece of heat treatable steel, it will be understood that the pincers 20 and 22 could be formed separately and secured in the above-described relationship by many well-known techniques such as clamping or brasing. Also, the pincers could be formed from any suitable structural material having the strength, resiliency and ability to hold a sharpened edge. The pincers should also be able to withstand common sterilizing procedures such as immersion in alcohol or a flame. Further, although the splinter puller 12 has been described as a two-piece instrument with a detachable handle, it should be understood that it could be manufactured from a single piece of material. However, the two-part construction is preferred since it allows the handle 18 to be manufactured from a material that is less costly than the heat treated steel forming the pincers 20 and 22 and the base portion 26. These and other modifications will become apparent to those skilled in the art from the foregoing description and accompanying drawings. Such modifications are intended to fall within the scope of the appended claims.

What is claimed is:

1. An instrument for removing a splinter embedded in skin comprising,
a handle extending in a first direction,
a pair of pincers secured at one end to one end of said handle and spaced in a second direction transverse to said first direction, said pincers being substantially broader in a third direction orthogonal to said first and second direction than in said second direction, and tapering convexly at their free ends in said second and third directions to tips, said tapering defining a leading edge adjacent each of said tips that are opposed to one another, said pincers being movable with respect to one another generally in the second direction to grip said splinter between said opposed leading edges, and said leading edges being sharpened to slice the skin in a direction generally normal to the sharpened leading edge in response to movement of the instrument in a direction at least in part parallel to said sharpened leading edges, said slicing facilitating the entry of the instrument into the skin to reach said splinter, the interior mutually facing surfaces of said free ends adjacent said leading edges being hollow to prevent contact between the pincers over said surfaces from blocking said gripping at said leading edges, and said hollows and said convex tapering of said free ends being structured to prevent the skin adjacent said splinter from blocking said gripping at said leading edges.

2. An instrument according to claim 1 in which each of said free ends extends between its leading edges in the third direction for at least 1/16 inch except for the portion immediately adjacent the tip of said pincer.

3. An instrument according to claim 1 in which one of said pair of pincers has a thinned region near said handle to promote movement of said pincer in said second direction, and the other of said pair of pincers is substantially stationary.

4. An instrument according to claim 1 wherein said pincers are bowed away from each other along said second direction to further reduce blocking.

* * * * *